(12) United States Patent
Shapiro

(10) Patent No.: US 8,198,442 B2
(45) Date of Patent: Jun. 12, 2012

(54) METHOD FOR PREPARATION OF OPTIONALLY 2-SUBSTITUTED 1,6-DIHYDRO-6-OXO-4-PYRIMIDINECARBOXYLIC ACIDS

(75) Inventor: Rafael Shapiro, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 841 days.

(21) Appl. No.: 11/886,605

(22) PCT Filed: Apr. 28, 2006

(86) PCT No.: PCT/US2006/016340
§ 371 (c)(1),
(2), (4) Date: Sep. 17, 2007

(87) PCT Pub. No.: WO2006/121648
PCT Pub. Date: Nov. 16, 2006

(65) Prior Publication Data
US 2009/0043098 A1 Feb. 12, 2009

Related U.S. Application Data

(60) Provisional application No. 60/678,264, filed on May 6, 2005.

(51) Int. Cl.
*C07D 239/28* (2006.01)
*C07D 239/42* (2006.01)
(52) U.S. Cl. .................. 544/319; 544/326; 544/334
(58) Field of Classification Search .................. 544/319, 544/326, 334
See application file for complete search history.

(56) References Cited

U.S. PATENT DOCUMENTS

| | | | |
|---|---|---|---|
| 4,666,915 A | 5/1987 | Ozeki et al. | |
| 5,324,710 A | 6/1994 | Ort et al. | |
| 5,525,724 A | 6/1996 | Hunds | |
| 5,654,311 A | 8/1997 | Kurtz et al. | |
| 5,859,020 A | 1/1999 | Preuss et al. | |
| 6,200,977 B1 | 3/2001 | Cushing et al. | |
| 6,281,358 B1 | 8/2001 | Meyer et al. | |
| 6,528,513 B2 | 3/2003 | Cushing et al. | |
| 6,559,307 B2 | 5/2003 | Meyer et al. | |
| 6,835,726 B2 | 12/2004 | Cushing et al. | |
| 7,863,220 B2 * | 1/2011 | Clark et al. | 504/225 |
| 2003/1130264 | 7/2003 | Jaen | |
| 2005/0059687 A1 | 3/2005 | Makings et al. | |
| 2007/0197391 A1 * | 8/2007 | Clark et al. | 504/236 |
| 2009/0054647 A1 | 2/2009 | Annis | |

FOREIGN PATENT DOCUMENTS

| | | |
|---|---|---|
| CA | 207185 A | 4/1991 |
| EP | 1200414 A1 | 5/2002 |
| EP | 1646615 A1 | 4/2006 |
| JP | 1991031267 A1 | 2/1991 |
| JP | 1991041071 A1 | 2/1991 |
| WO | 91/06541 A | 5/1991 |
| WO | 92/05159 | 4/1992 |
| WO | 99/41253 A | 8/1999 |
| WO | 02/064096 A3 | 8/2002 |
| WO | WO 2004/111014 A1 | 12/2004 |
| WO | 2005063721 A1 | 7/2005 |
| WO | WO 2006/097220 A1 | 9/2006 |
| WO | WO 2006/083012 A1 | 11/2006 |
| WO | WO 00/63183 A1 | 10/2009 |

OTHER PUBLICATIONS

G. D. Daves, Jr. et al., Pyrimidines. II. Orotic Acid Analogs, J. Org. Chem., 1961, vol. 26:2755-2763.

* cited by examiner

*Primary Examiner* — Venkataraman Balasubramanian

(57) ABSTRACT

A new method for the preparation of optionally 2-substituted 1,6-dihydro-6-oxo-4-pyrimidinecarboxylic acid compound of Formula 1 is disclosed

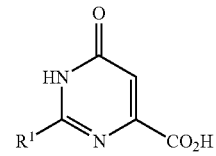

wherein $R^1$ is H or an optionally substituted carbon moiety.

18 Claims, No Drawings

METHOD FOR PREPARATION OF OPTIONALLY 2-SUBSTITUTED 1,6-DIHYDRO-6-OXO-4-PYRIMIDINECARBOXYLIC ACIDS

This application is a national filing under 35 U.S.C. §371 of International Application No. PCT/US2006/016340 filed Apr. 28, 2006 and claims priority to U.S. Provisional Application No. 60/678,264 filed May 6, 2005.

FIELD OF THE INVENTION

A new method for the preparation of optionally 2-substituted 1,6-dihydro-6-oxo-4-pyrimidinecarboxylic acids is disclosed.

BACKGROUND OF THE INVENTION

G. D. Daves, Jr. et al. (*J. Org. Chem.*, 1961, 26, 2755) disclose a preparation of 1,6-dihydro-6-oxo-4-pyrimidinecarboxylic acid by cyclocondensation of diethyl oxalacetate with formamidine in aqueous NaOH. In their procedure, the components were combined all at once without particular control of pH to provide a yield of 63%. Other reports on similar condensations using oxalacetate diesters disclose even lower yields. Therefore new methods are needed to provide higher yields as well as affording low cost, high efficiency, and reliability.

SUMMARY OF THE INVENTION

This invention provides a method for preparing a 1,6-dihydro-6-oxo-4-pyrimidinecarboxylic acid compound of Formula 1

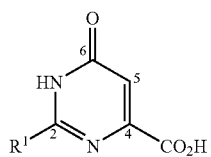

1 wherein $R^1$ is H or an optionally substituted carbon moiety; comprising the steps of:

(1) contacting a mixture comprising (a) a compound of Formula 2a

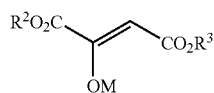

2a wherein M is alkali metal and $R^2$ and $R^3$ are independently $C_1$-$C_4$ alkyl, (b) a $C_1$-$C_4$ alkanol, and (c) a first portion of water, with a solution comprising a first base and a second portion of water, said base being in an amount sufficient to create a first resultant solution having a pH ranging from about 10 to about 14, said first resultant solution comprising a compound of Formula 2b,

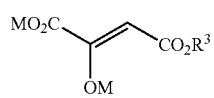

2b wherein M and $R^3$ are defined as above for Formula 2a;

(2) contacting the first resultant solution comprising the compound of Formula 2b with a compound of Formula 3 or an acid salt thereof or with a solution comprising a compound of Formula 3 or an acid salt thereof,

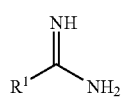

3 wherein $R^1$ is defined as above for Formula 1, and a second base in an amount sufficient to create a second resultant solution having a pH ranging from about 9 to about 12, said second resultant solution comprising a salt of the compound of Formula 1; and (3) adding an acid to the second resultant solution comprising the salt of the compound of Formula 1 to form the compound of Formula 1.

The invention also provides a method for preparing the compound of Formula 4

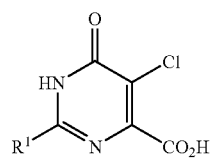

4 wherein $R^1$ is H or an optionally substituted carbon moiety, comprising the aforedescribed method and an additional step of contacting the compound of Formula 1 with a chlorinating agent.

The invention also provides a method for preparing the compound of Formula 6

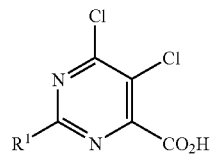

6 wherein $R^1$ is H or an optionally substituted carbon moiety, comprising the aforedescribed method and an additional step of contacting the compound of Formula 4 with a chloride displacement agent.

The invention also provides a method for preparing the compound of Formula 7

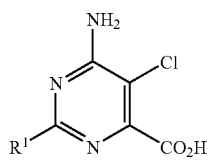

7 wherein R¹ is H or an optionally substituted carbon moiety, comprising the aforedescribed method and an additional step of contacting the compound of Formula 6 with ammonia.

The invention also provides a method for preparing the compound of Formula 8

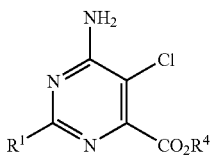

8 wherein R¹ is H or an optionally substituted carbon moiety; and R⁴ is an optionally substituted carbon moiety; comprising the aforedescribed method and an additional step of contacting the compound of Formula 7 with an R⁴ transfer agent.

Accordingly, the invention also provides a method for preparing a compound of Formula 4 using a compound of Formula 1, characterized by preparing the compound of Formula 1 from the compounds of Formulae 2a and 3 by the aforedescribed method. The invention also provides a method for preparing a compound of Formula 6 using a compound of Formula 1, characterized by preparing the compound of Formula 1 from the compounds of Formulae 2a and 3 by the aforedescribed method. The invention also provides a method for preparing a compound of Formula 7 using a compound of Formula 1, characterized by preparing the compound of Formula 1 from the compounds of Formulae 2a and 3 by the aforedescribed method. The invention also provides a method for preparing a compound of Formula 8 using a compound of Formula 1, characterized by preparing the compound of Formula 1 from the compounds of Formulae 2a and 3 by the aforedescribed method.

DETAILED DESCRIPTION OF THE INVENTION

In the recitations herein, the term "carbon moiety" refers to a radical comprising a carbon atom linking the radical to the remainder of the molecule. As the substituent R¹ is separated from the reaction center and R⁴ is added at the end of the disclosed sequence of steps, R¹ and R⁴ can encompass a great variety of carbon-based groups preparable by modern methods of synthetic organic chemistry. "Carbon moiety" thus includes alkyl, alkenyl and alkynyl, which can be straight-chain or branched. "Carbon moiety" also includes carbocyclic and heterocyclic rings, which can be saturated, partially saturated, or completely unsaturated. Furthermore, unsaturated rings can be aromatic if Hückel's rule is satisfied. The carbocyclic and heterocyclic rings of a carbon moiety can form polycyclic ring systems comprising multiple rings connected together. The term "carbocyclic ring" denotes a ring wherein the atoms forming the ring backbone are selected only from carbon. The term "heterocyclic ring" denotes a ring wherein at least one of the ring backbone atoms is other than carbon. "Saturated carbocyclic" refers to a ring having a backbone consisting of carbon atoms linked to one another by single bonds; unless otherwise specified, the remaining carbon valences are occupied by hydrogen atoms. The term "aromatic ring system" denotes fully unsaturated carbocycles and heterocycles in which at least one ring in a polycyclic ring system is aromatic. Aromatic indicates that each of ring atoms is essentially in the same plane and has a p-orbital perpendicular to the ring plane, and in which (4n+2)π electrons, when n is 0 or a positive integer, are associated with the ring to comply with Hückel's rule. The term "aromatic carbocyclic ring system" includes fully aromatic carbocycles and carbocycles in which at least one ring of a polycyclic ring system is aromatic. The term "nonaromatic carbocyclic ring system" denotes fully saturated carbocycles as well as partially or fully unsaturated carbocycles wherein none of the rings in the ring system are aromatic. The terms "aromatic heterocyclic ring system" and "heteroaromatic ring" include fully aromatic heterocycles and heterocycles in which at least one ring of a polycyclic ring system is aromatic. The term "nonaromatic heterocyclic ring system" denotes fully saturated heterocycles as well as partially or fully unsaturated heterocycles wherein none of the rings in the ring system are aromatic. The term "aryl" denotes a carbocyclic or heterocyclic ring or ring system in which at least one ring is aromatic, and the aromatic ring provides the connection to the remainder of the molecule.

The carbon moieties specified for R¹ and R⁴ are optionally substituted. The term "optionally substituted" in connection with these carbon moieties refers to carbon moieties that are unsubstituted or have at least one non-hydrogen substituent. Similarly, the term "optionally substituted" in connection with alkyl and tertiary alkyl refers to alkyl and tertiary alkyl radicals that are unsubstituted or have a least one non-hydrogen substituent. Illustrative optional substituents include alkyl, alkenyl, cycloalkyl, cycloalkenyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, cycloalkoxy, aryloxy, alkylthio, alkenylthio, alkynylthio, cycloalkylthio, arylthio, alkylsulfinyl, alkenylsulfinyl, alkynylsulfinyl, cycloalkylsulfinyl, arylsulfinyl, alkylsulfonyl, alkenylsulfonyl, alkynylsulfonyl, cycloalkylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyl, alkenylaminocarbonyl, alkynylaminocarbonyl, arylaminocarbonyloxy, alkoxycarbonylamino, alkenyloxycarbonylamino, alkynyloxycarbonylamino and aryloxycarbonylamino, each further optionally substituted; and halogen, cyano and nitro. The optional further substituents are independently selected from groups like those illustrated above for the substituents themselves to give additional substituent radicals for R¹ and R⁴ such as haloalkyl, haloalkenyl and haloalkoxy. As a further example, alkylamino can be further substituted with alkyl, giving dialkylamino. The substituents can also be tied together by figuratively removing one or two hydrogen atoms from each of two substituents or a substituent and the supporting molecular structure and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—CH₂—O—. Tying together a hydroxy group and the molecular structure to which it is attached can give cyclic ethers, including epoxides. Illustrative substituents also include oxygen, which when attached to carbon forms a carbonyl function. Similarly, sulfur when attached to carbon forms a thiocarbonyl function.

As referred to herein, "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadienyl. "Alkoxy" includes, for example, methoxy, ethoxy, n-propyloxy, isopropyloxy and the different butoxy, pentoxy and hexyloxy isomers. "Alkoxyalkyl" includes, for example, $CH_3OCH_2$, $CH_3OCH_2CH_2$, $CH_3CH_2OCH_2$, $CH_3CH_2OCH_2CH_2$. "Hydroxyalkyl" includes, for example, $HOCH_2CH_2CH_2$, $CH_3CH(OH)CH_2CH_2$, $CH_3CH(OH)CH_2$. "Alkenyloxy" includes straight-chain- or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "alkenylthio", "alkenylsulfinyl", "alkenylsulfonyl", "alkynylthio", "alkynylsulfinyl", "alkynylsulfonyl", and the like, are defined analogously to the above examples. Examples of "alkylcarbonyl" include $C(O)CH_3$, $C(O)CH_2CH_3$ and $C(O)CH(CH_3)_2$. Examples of "alkoxycarbonyl" include $CH_3OC(=O)$, $CH_3CH_2C(=O)$, $CH_3CH_2CH_2OC(=O)$, $(CH_3)_2CHOC(=O)$ and the different butoxy- or pentoxycarbonyl isomers. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)(cycloalkyl)amino" means a cycloalkylamino group where the amino hydrogen atom is replaced by an alkyl radical; examples include groups such as (methyl)(cyclopropyl)amino, (butyl)(cyclobutyl)amino, (propyl)cyclopentylamino, (methyl)cyclohexylamino and the like. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$.

The total number of carbon atoms in a substituent group is indicated by the "$C_i$-$C_j$" prefix where i and j are, for example, numbers from 1 to 3; e.g., $C_1$-$C_3$ alkyl designates methyl through propyl.

Although there is no definite limit to the size of $R^1$ and $R^4$, optionally substituted alkyl moieties of $R^1$ commonly include 1 to 6 carbon atoms, more commonly 1 to 4 carbon atoms and most commonly 1 to 3 carbon atoms in the alkyl chain. Optionally substituted alkyl moieties of $R^4$ commonly include 1 to 14 carbon atoms, more commonly 1 to 8 carbon atoms and most commonly 1 to 4 carbon atoms in the alkyl chain. Optionally substituted alkenyl and alkynyl moieties of $R^1$ commonly include 2 to 6 carbon atoms, more commonly 2 to 4 carbon atoms and most commonly 2 to 3 carbon atoms in the alkenyl or alkynyl chain. Optionally substituted alkenyl and alkynyl moieties of $R^4$ commonly include 2 to 14 carbon atoms, more commonly 3 to 8 carbon atoms and most commonly 3 to 4 carbon atoms in the alkenyl or alkynyl chain.

As indicated above, the carbon moieties of $R^1$ and $R^4$ may be an aromatic ring or ring system. Examples of aromatic rings or ring systems include a phenyl ring, 5- or 6-membered heteroaromatic rings, 3- to 8-membered saturated or unsaturated carbocyclic ring systems, aromatic 8-, 9- or 10-membered fused carbobicyclic ring systems and aromatic 8-, 9- or 10-membered fused heterobicyclic ring systems wherein each ring or ring system is optionally substituted. The term "optionally substituted" in connection with these $R^1$ and $R^4$ carbon moieties refers to carbon moieties which are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four.

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Combining chemicals and adding chemicals refers to contacting the chemicals with each other.

Numeric ranges are inclusive of each and every integer value defining the range.

One skilled in the art also recognizes that the compounds of Formulae 1 and 4 are in equilibrium with their respective tautomeric counterparts of Formulae 1a and 4a, as shown in Exhibit 1.

Exhibit 1

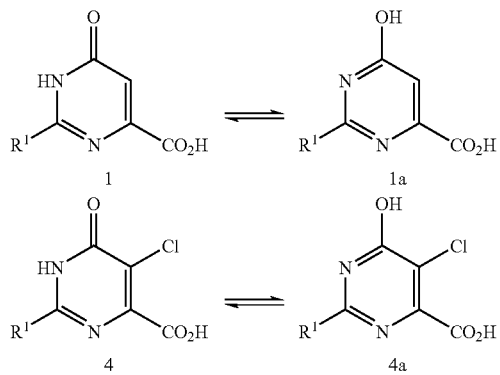

Unless expressly stated otherwise, references to Formulae 1 and 4 in the present disclosure and claims are to be construed to include all tautomers, including Formulae 1a and 4a, respectively.

The nitrogen atom in the compounds of Formulae 1, 3, 4, 6, 7 and 8 (including 1a and 4a) can be protonated, allowing said compounds to form acid-addition salts with inorganic or organic acids including but not limited to hydrobromic, hydrochloric, nitric, phosphoric, sulfuric, or 4-toluenesulfonic acids.

Embodiments of the present invention include:

Embodiment A1. A method as set forth in the Summary of the Invention wherein $R^1$ is an optionally substituted carbon moiety.

Embodiment A2. A method of Embodiment A1 wherein $R^1$ is optionally substituted cyclopropyl or an optionally substituted phenyl.

Embodiment A3. A method of Embodiment A2 wherein $R^1$ is optionally substituted cyclopropyl.

Embodiment A4. A method of Embodiment A2 wherein $R^1$ is optionally substituted phenyl.

Embodiment A5. A method of Embodiment A3 wherein $R^1$ is unsubstituted cyclopropyl.

Embodiment A6. A method of Embodiment A4 wherein $R^1$ is phenyl substituted at the para position and optionally substituted at other positions.

Embodiment A7. A method of Embodiment A6 wherein $R^1$ is phenyl substituted with Br or Cl at the para position and optionally substituted with 1-2 halogen at other positions.

Embodiment A8. A method of Embodiment A7 wherein $R^1$ is phenyl substituted with Br or Cl at the para position.

Embodiment A9. A method as set forth in the Summary of the hIvention wherein $R^4$ is $C_1$-$C_{14}$ alkyl, $C_2$-$C_{14}$ alkoxyalkyl, $C_2$-$C_{14}$ hydroxyalkyl or benzyl.

Embodiment A10. A method of Embodiment A9 wherein $R^4$ is $C_1$-$C_{14}$ alkyl, $C_2$-$C_{14}$ alkoxyalkyl or $C_2$-$C_{14}$ hydroxyalkyl.

Embodiment A11. A method of Embodiment A10 wherein $R^4$ is $C_1$-$C_8$ alkyl, $C_2$-$C_8$ alkoxyalkyl or $C_2$-$C_8$ hydroxyalkyl.

Embodiment A12. A method of Embodiment A11 wherein $R^4$ is $C_1$-$C_8$ alkyl or $C_2$-$C_8$ alkoxyalkyl.

Embodiment A13. A method of Embodiment A12 wherein $R^4$ is $C_1$-$C_4$ alkyl.

Embodiment B1. A method as set forth in the Summary of the Invention wherein the alkanol is methanol or ethanol.

Embodiment B2. A method of Embodiment B1 wherein the alkanol is ethanol.

Embodiment B3. A method as set forth in the Summary of the Invention wherein the volume ratio of the first portion of water to the compound of Formula 2a ranges from about 10 to about 0.01.

Embodiment B4. A method of Embodiment B3 wherein the volume ratio of the first portion of water to the compound of Formula 2a ranges from about 6 to about 1.

Embodiment B5. A method of Embodiment B4 wherein the volume ratio of the first portion of water to the compound of Formula 2a ranges from about 3 to about 2.

Embodiment B6. A method as set forth in the Summary of the hIvention wherein the volume ratio of the first portion of water to the alkanol ranges from about 0.01 to about 100.

Embodiment B7. A method of Embodiment B6 wherein the volume ratio of the first portion of water to the alkanol ranges from about 1 to about 50.

Embodiment B8. A method of Embodiment B7 wherein the volume ratio of the first portion of water to the alkanol ranges from about 5 to about 10.

Embodiment B9. A method as set forth in the Summary of the Invention wherein the first base is an alkali metal hydroxide.

Embodiment B10. A method of Embodiment B9 wherein the alkali metal hydroxide is sodium hydroxide or potassium hydroxide.

Embodiment B11. A method of Embodiment B10 wherein the alkali metal hydroxide is sodium hydroxide.

Embodiment B12. A method of Embodiment B9 wherein the molar ratio of the first base to the compound of Formula 2a ranges from about 0.5 to about 2.

Embodiment B13. A method of Embodiment B12 wherein the molar ratio of the first base to the compound of Formula 2a ranges from about 0.7 to about 1.5.

Embodiment B14. A method of Embodiment B13 wherein the molar ratio of the first base to the compound of Formula 2a is in a range of about 0.9 to about 1.2.

Embodiment B15. A method as set forth in the Summary of the Invention wherein the pH of the first resultant solution is in a range of about 11 to about 13.

Embodiment B16. A method as set forth in the Summary of the Invention wherein step (1) is conducted at a temperature in a range of about 5 to about 40° C.

Embodiment B17. A method of Embodiment B16 wherein the temperature is in a range of about 20 to about 30° C.

Embodiment C1. A method as set forth in the Summary of the Invention wherein the first resultant solution comprising the compound of Formula 2b is contacted with the compound of Formula 3 or an acid salt thereof.

Embodiment C2. A method as set forth in the Summary of the Invention wherein the molar ratio of the compound of Formula 3 or an acid salt thereof to the compound of Formula 2a is in a range of about 0.6 to about 1.2.

Embodiment C3. A method of Embodiment C2 wherein the molar ratio of the compound of Formula 3 or an acid salt thereof to the compound of Formula 2a is in a range of about 0.6 to about 1.0.

Embodiment C4. A method of Embodiment C3 wherein the molar ratio of the compound of Formula 3 or an acid salt thereof to the compound of Formula 2a is in a range of about 0.7 to about 0.9.

Embodiment C5. A method as set forth in the Summary of the Invention wherein the second base is an alkali metal hydroxide.

Embodiment C6. A method of Embodiment C5 wherein the alkali metal hydroxide is sodium hydroxide or potassium hydroxide.

Embodiment C7. A method of Embodiment C6 wherein the alkali metal hydroxide is sodium hydroxide.

Embodiment C8. A method of Embodiment C5 wherein the molar ratio of the second base to the compound of Formula 3 is in a range of about 2 to about 0.5.

Embodiment C9. A method of Embodiment C8 wherein the molar ratio of the second base to the compound of Formula 3 is in a range of about 1.2 to about 0.8.

Embodiment C10. A method as set forth in the Summary of the Invention wherein the pH of the second resultant solution is in a range of about 9 to about 12.

Embodiment C11. A method of Embodiment C10 wherein the pH ranges from about 10.5 to about 11.5.

Embodiment C12. A method as set forth in the Summary of the Invention wherein step (2) is conducted at a first temperature in a range of about 0 to about 40° C., and later increased to a second temperature in a range of about 10 to about 70° C.

Embodiment C13. A method of Embodiment C12 wherein the first temperature is in a range of about 20 to about 40° C., and the second temperature is in a range of about 50 to about 65° C.

Embodiment D1. A method as set forth in the Summary of the Invention wherein the acid added in step (3) is a mineral acid.

Embodiment D2. A method of Embodiment D1 wherein the acid is sulfuric acid or hydrochloric acid.

Embodiment D3. A method as set forth in the Summary of the Invention wherein after the addition of the acid in step (3), the second resulting solution has a pH in a range of below about 3.

Embodiment D4. A method of Embodiment D3 wherein the pH is in a range of about 1 to about 2.

Embodiment D5. A method as set forth in the Summary of the Invention wherein step (3) is conducted at a first temperature in a range of about 30 to about 55° C., and later decreased to a second temperature in a range of about 0 to about 20° C.

Embodiment D6. A method of Embodiment D5 wherein the first temperature is in a range of about 40 to about 45° C., and the second temperature is in a range of about 0 to about 10° C.

Embodiment E1. A method as set forth in the Summary of the Invention preparing the compound of Formula 4 wherein the chlorinating agent is selected from the group consisting of chlorine, hypochlorous acid, sulfuryl chloride, sodium hypochlorite, calcium hypochlorite and potassium hypochlorite.

Embodiment E2. A method as set forth in the Summary of the Invention preparing the compound of Formula 6 wherein the chloride displacement agent is selected from the group consisting of phosphorus oxychloride, thionyl chloride, oxalyl chloride, phosgene, diphosgene and triphosgene.

In the following Schemes 1-6 the definitions of $R^1$, $R^2$, $R^3$ and $R^4$ in the compounds of Formulae 1 through 8 are as defined above in the Summary of the Invention and description of Embodiments unless otherwise indicated.

The present method for preparing optionally 2-substituted 1,6-dihydro-6-oxo-4-pyrimidinecarboxylic acid compounds of Formula 1 is illustrated in Schemes 1 and 2. As shown in Scheme 1, in the first step a mixture comprising an oxalacetate diester salt of Formula 2a, a lower alkanol (i.e. $C_1$-$C_4$ alkanol) and water is combined with a solution comprising a base dissolved in water. The base is present in sufficient amount such that the resulting solution comprising the salt of Formula 2b has a pH ranging from about 10 to about 14. In this pH range the ester group germinal to the OM on Formula 2a is believed to be selectively saponified to form the corresponding $CO_2M$ group of Formula 2b.

Scheme 1

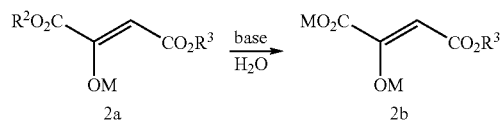

wherein M is alkali metal and $R^2$ and $R^3$ are independently $C_1$-$C_4$ alkyl.

Typically the mixture comprising an oxalacetate diester salt of Formula 2a, $C_1$-$C_4$ alkanol and water is formed by adding the salt of Formula 2a to a mixture of the $C_1$-$C_4$ alkanol and water, but other orders of addition are possible. Furthermore the oxalacetate diester salt of Formula 2a can be prepared in situ by combining the corresponding oxalacetate diester with the alkanol and/or water containing about one equivalent of sodium or potassium hydroxide or alkoxide. The mixture comprising the oxalacetate diester salt of Formula 2a, $C_1$-$C_4$ alkanol and water is typically present as a solution wherein the oxalacetate diester salt of Formula 2a is entirely dissolved but depending on amounts of alkanol and water can also be a suspension wherein some of the oxalacetate diester salt of Formula 2a remains undissolved. While the potassium salt of Formula 2a works satisfactorily for this method, the sodium salt is preferred, as it is conveniently prepared in excellent yield. Although a wide range of carbon-bearing moieties can be used as $R^2$ and $R^3$, for reason of cost and convenience, lower alkyl (i.e. $C_1$-$C_4$ alkyl) groups, i.e. methyl, ethyl, n-propyl, isopropyl, n-butyl, sec-butyl or tent-butyl, are most satisfactory, and short alkyl groups such as ethyl work well.

The $C_1$-$C_4$ alkanol is selected from the possible $C_1$-$C_4$ alkanols, i.e. methanol, ethanol, n-propanol, isopropanol, n-butanol, sec-butanol, tert-butanol, and their mixtures. Ethanol, optionally containing denaturing alcohols such as isopropanol, has been found to work well for this reaction, but other $C_1$-$C_4$ alkanols such as methanol can be used. As the mixture comprises water, ethanol can be conveniently used as its 95% ethanol-5% water azeotrope. Typically the volume ratio of the water to the compound of Formula 2a in the mixture before addition of the base ranges from about 0.01 to about 10, more typically from about 1 to about 6, and most typically from about 2 to about 3. Most typically the volume ratio of the water-alkanol mixture to the compound of Formula 2a in the mixture before addition of the base ranges from about 2 to about 6. Typically the volume ratio of the water to the alkanol in the mixture before addition of the base ranges from about 0.01 to about 100, more typically from about 1 to about 50, and most typically from about 5 to about 10. When ethanol is used as the $C_1$-$C_4$ alkanol, about 2.5 volumes of a mixture of about 15 wt % ethanol in water relative to the compound of Formula 2a works well.

The mixture comprising the oxalacetate diester salt of Formula 2a, $C_1$-$C_4$ alkanol and water is combined with a solution of a base in water. Preferably the aqueous solution of the base is added to the mixture comprising oxalacetate diester salt of Formula 2a, $C_1$-$C_4$ alkanol and water, as this order of addition prevents the compound of Formula 2a from being temporarily exposed to excessive base. The base needs to be strong enough to provide a pH in the range of about 10 to 14. Most conveniently and inexpensively the base is an alkali metal hydroxide, such as sodium or potassium hydroxide. Typically about 0.5 to about 2, more typically about 0.7 to about 1.5, and most typically about 0.9 to 1.2 molar equivalents of the base is used relative to the compound of Formula 2a. This amount of base is believed to saponify the compound of Formula 2a to form the compound of Formula 2b while providing a final pH in the range of about 10 to 14. Preferably the amount of base is selected so that the final pH is in the range between about 11 and 13.

The base is added as a water solution to the mixture comprising the oxalacetate diester salt of Formula 2a, $C_1$-$C_4$ alkanol and water. Typically the water solution of the base comprises about 1 to 50 wt % of base, more typically about 10 to 40 wt. % of base, and most typically about 20 to 30 wt % of base. During the addition of the aqueous base solution the temperature of the reaction mixture is typically maintained between about 5 and 40° C., and more typically about 20 to 30° C. (e.g., about 25° C.).

The method of Scheme 1 forms a hydrolysate mixture containing predominately the monoalkyl oxalacetate salt compound of Formula 2b, generally in the form of a solution. This solution is typically used directly in unrefined form in the next step. Although the intermediate monoalkyl oxalacetate salt compound of Formula 2b is typically not isolated, based on the high yields for the overall method, yields of the compound of Formula 2b from the step shown as Scheme 1 are reasonably believed to be on the order of 80 to 90%.

As shown in Scheme 2, in the next step the compound of Formula 1 is prepared by contacting the hydrolysate mixture comprising the compound of Formula 2b formed in the first step with a carboximidamide of Formula 3.

Scheme 2

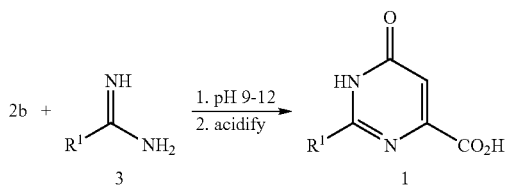

Typically about 0.6 to about 1.2, more typically about 0.6 to about 1, most typically about 0.7 to about 0.9 molar equivalents of the carboximidamide of Formula 3 is employed relative to the dialkyl ester of Formula 2a used to prepare the intermediate compound of Formula 2b. The carboximidamide of Formula 3 can be either in the form of its free base or in the form of a salt such as its hydrochloride salt. Although the hydrolysate mixture can be added to the carboximidamide of Formula 3, typically the carboximidamide is added to the hydrolysate mixture. The carboximidamide can be contacted directly with the hydrolysate mixture, or it can be added as a solution in a suitable solvent, such as water or a lower alkanol.

Typically the carboximidamide of Formula 3 is contacted with the hydrolysate mixture at a temperature between about 0 and about 40° C., more typically between about 20 to about 40° C., preferably between about 20 to about 30° C. As is discussed below, the temperature is often subsequently raised to accelerate completion of the reaction.

For this reaction step the solution formed needs to have a pH in the range from about 9 to about 12, preferably about 10 to about 12, more preferably about 10.5 to about 11.5. A sufficient amount of base is thus added to provide this pH range. If the carboximidamide of Formula 3 is used in the form of its free base, the amount of additional base needed to achieve the range of about 9 to 12 can be zero. However, if the carboximidamide of Formula 3 is in the form of a salt, such as its hydrochloride salt, a sufficient amount of base is needed to provide the needed pH range. Although the base can be added to the carboximidamide salt or a solution thereof before adding the carboximidamide to the hydrolysate mixture, or the base can be added to the hydrolysate mixture before adding the carboximidamide salt, preferably the base is added to the hydrolysate mixture after addition of the carboximidamide salt. The base needs to be sufficiently strong to provide the needed pH; an alkali metal hydroxide such as sodium or potassium hydroxide works well for this purpose. When the carboximidamide of Formula 3 is in the form of a salt, the molar equivalents of the base relative to the carboximidamide is typically in the range of about 0.5 to about 2, and more typically in the range of about 0.8 to about 1.2. Typically the base is dissolved in a solvent such as water before addition to the reaction mixture.

After the carboximidamide of Formula 3 is combined with the hydrolysate mixture together with an amount of base needed to provide a pH range of about 9 to 12 in the reaction mixture, the reaction mixture is often warmed to accelerate completion of the reaction. For this purpose the temperature is typically adjusted to about 10 to about 70° C., and more typically to about 50 to about 65° C.

The reaction forms the compound of Formula 1 as its carboxylate salt, which generally is dissolved in the reaction mixture. To isolate the compound of Formula 1, the reaction mixture is typically cooled to a temperature of about 55° C. or lower (e.g., between about 30 and 55° C., often conveniently about 45° C.), and an acid is added to acidify the reaction mixture and convert the compound of Formula 1 from its carboxylate salt to its free acid form. The usual common mineral acids such as hydrochloric acid, sulfuric acid or phosphoric acid work well. The acid is added in sufficient amount to lower the pH of the reaction mixture below about 3, typically in the range of about 1 to about 2. Often under these conditions the product of Formula 1 will crystallize. The reaction mixture is then preferably cooled to the range of about 0 to about 10° C. to promote crystallization, and the solid product is collected by filtration, washing and drying. If the product of Formula 1 does not form a solid, it can be isolated by extracting the reaction mixture with a suitable water-immiscible solvent such as ether, dichloromethane or ethyl acetate, drying, and evaporating the solvent.

The method of Schemes 1 and 2 is illustrated in Step B of Example 1. The carboximidamide compounds of Formula 3 can be prepared by methods known in the art, including the improved modifications taught in U.S. Pat. Nos. 4,323,570 and 4,012,506. The preparation of a compound of Formula 3 is illustrated in Step A of Example 1.

Thus 1,6-dihydro-6-oxo-4-pyrimidinecarboxylic acid compounds of Formula 1 can be conveniently prepared in good yield from compounds of Formula 2a and 3 according to the aforedescribed method. The 1,6-dihydro-6-oxo-4-pyrimidinecarboxylic acid compounds of Formula 1 prepared by this method can then be transformed using further reaction steps into a variety of optionally substituted 4-pyrimidinecarboxylic acids and esters.

The first subsequent reaction, shown in Scheme 3, prepares a compound of Formula 4 by contacting the compound of Formula 1 with a chlorinating agent.

Scheme 3

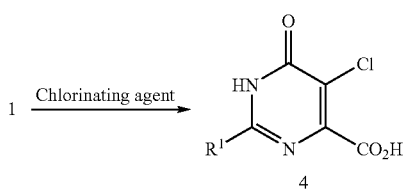

This method involves the replacement of the hydrogen at the 4-position on the 1,6-dihydro-6-oxo-4-pyrimidinyl ring with chlorine. As is known in the art, a variety of chlorinating agents (i.e. reagents that replace hydrogen atoms in organic molecules with chlorine) can be used for this type of transformation. Described below are illustrative procedures for the method when the chlorinating agent is chlorine, hypochlorous acid, sulfinyl chloride or inorganic hypochlorite such as sodium hypochlorite, calcium hypochlorite and potassium hypochlorite.

In one procedure, a compound of Formula 1 is suspended in an inert solvent, typically about 3 to 6 volumes of water, optionally containing 0.5 to 3.5 molar equivalents of mineral acid, preferably hydrochloric acid. About 0.95 to about 1.2 molar equivalents of a chlorinating agent, preferably chlorine or hypochlorous acid (HOCl), is added with good agitation at about 10 to about 35° C. If hypochlorous acid is used, it can be generated in situ by adding at least 1 molar equivalent of mineral acid to the suspension of the compound of Formula 1 prior to adding an inorganic hypochlorite, preferably sodium hypochlorite (NaOCl) as typically a 5 to 14% aqueous solution. Excess chlorinating agent can be removed by purging with an inert gas or by adding a reducing agent such as sodium sulfite. If the product of Formula 4 forms a solid, it can be isolated by filtration. If the product of Formula 4 does not form a solid, it can be isolated by extraction of the aqueous reaction mixture with a water-immiscible solvent, such as ether, dichloromethane or ethyl acetate, drying, and evaporating the extraction solvent. This procedure is illustrated in Step C1 of Example 1.

In another procedure, the compound of Formula 1 is dissolved in an inert solvent, preferably about 1.5 to about 4 volumes of water, optionally containing about 0 to 3.5 molar equivalents of inorganic base, preferably sodium hydroxide or potassium hydroxide. About 0.95 to about 1.2 molar equivalents of a chlorinating agent, preferably chlorine or sodium hypochlorite (NaOCl, typically as a 5 to 14% aqueous solution), is added with good agitation to the reaction mixture at about 0 to 70° C., typically about 10 to 35° C. When sodium hypochlorite is used as chlorinating agent, the amount of base is preferably about 0.85 to 1.2 molar equivalents relative to the compound of Formula 1. Excess chlorinating agent can be removed by purging with an inert gas or by adding a reducing agent such as sodium sulfite. The reaction mixture is then acidified by adding a mineral acid, such as concentrated hydrochloric acid, to lower the pH to about 0.5 to 3 and produce the free acid form of the compound of Formula 4. If the product of Formula 4 is a solid, it can be isolated by filtering. If the product of Formula 4 is not a solid, it can be isolated by extraction of the aqueous reaction mixture with a water-immiscible solvent, such as ether, dichloromethane or ethyl acetate, drying, and evaporating the extraction solvent. This procedure is illustrated in Step C2 of Example 1.

The second subsequent reaction, shown in Scheme 4, prepares a compound of Formula 6 by contacting the compound of Formula 4 with a chloride displacement agent.

Scheme 4

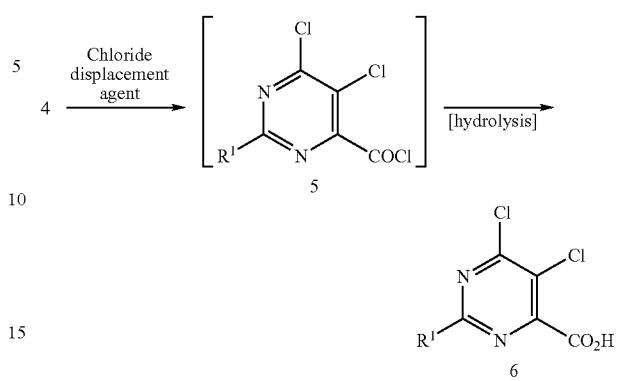

This method involves the replacement of the 6-oxo function on the 1,6-dihydro-6-oxo-4-pyrimidinyl ring with chlorine. As is known in the art, a variety of chloride displacement agents (i.e. reagents that replace hydroxy moieties in organic molecules with chlorine) can be used for this type of transformation. As the hydroxyl moiety on the carboxylic acid function can also be replaced by chlorine, contact with chloride displacement agents often results in formation of intermediate acyl chlorides of Formula 5, wherein $R^1$ is H or an optionally substituted carbon moiety, which are hydrolyzed on contact with water during reaction work up to provide the compounds of Formula 6. Described below are illustrative procedures for the method when the chloride displacement agent is phosphorus oxychloride, thionyl chloride, oxalyl chloride, phosgene, diphosgene or triphosgene.

In one procedure, a compound of Formula 4 is combined with about 2 to about 4 molar equivalents of chloride displacement agent such as phosphorus oxychloride. Optionally about 0.05 to 1.0 molar equivalents of N,N-dimethylformamide (DMF), typically without added solvent, is also included in the reaction mixture. The reaction mixture is maintained at a temperature between about 10 and about 100° C., typically between about 70 and about 95° C. Excess phosphorus oxychloride can be conveniently removed by distillation at a pressure of about 6 to 30 kPa. The reaction mixture (believed to consist of the acid chloride intermediate of Formula 5 and polymeric chlorophosphoric acids) is then carefully added to water optionally containing about 20 to 40% of a water-miscible organic co-solvent, preferably tert-butanol. About 25 wt % of tert-butanol in the mixture works well. If the product of Formula 6 is a solid, the resulting mixture can be further diluted with water to promote crystallization. The suspension of the crystalline product of Formula 6 is then filtered, washed with water, and typically dried. If the product of Formula 6 does not form a solid, it can be isolated by extracting the reaction mixture with a suitable water-immiscible solvent such as ether, dichloromethane or ethyl acetate and drying the solution. The solvent can be evaporated to isolate the compound of Formula 6, or if the solvent is suitable for the next reaction, the solution can be used directly. This procedure is illustrated in Step D1 of Example 1.

In another procedure, a compound of Formula 4 is mixed with about 2 to 4 volumes of an aprotic organic solvent, such as ethyl acetate, tetrahydrofuran or 1,2-dichloroethane, optionally about 0.02 to 0.2 molar equivalents of N,N-dimethylformamide, and about 2.0 to about 3.0 molar equivalents of a chloride displacement agent, preferably thionyl chloride, oxalyl chloride or phosgene. The reaction mixture is maintained at typically about 20 to 100° C., preferably at about 50 to 70° C., for typically 2 to 12 h. The reaction mixture (believed to consist of the acid chloride intermediate of Formula 5) is then carefully added to water with agitation. The product of Formula 6 can be isolated or a solution formed as described for the first procedure. The present procedure is illustrated in Step D2 of Example 1.

The third subsequent reaction, shown in Scheme 5, prepares a compound of Formula 7 by contacting the compound of Formula 6 with ammonia.

Scheme 5

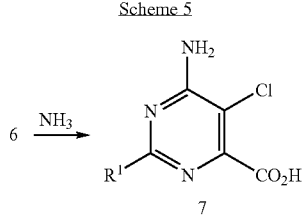

This method involves the replacement of the chlorine at the 6-position on the pyrimidinyl ring with an amino function. As is known in the art, this type of transformation generally involves contact of 6-chloropyrimidine compounds with ammonia. Typically the ammonia is provided from a supply cylinder or as a concentrated solution in a solvent (e.g., ammonium hydroxide), although ammonia can also be formed in situ by contact of ammonium salts such as ammonium chloride or ammonium sulfate with bases. Described below is an illustrative procedure.

In this procedure, a compound of Formula 6 is mixed with ammonia in a solvent. Although only about 1 molar equivalent of ammonia is stoichiometrically needed if another base is present, typically ammonia is the only base present and 3 to 7 molar equivalents of ammonia are used to obtain a rapid reaction rate. A wide variety of inert solvents can be used, including water, alkanols such as ethanol, and ethers such as tetrahydrofuran; water is inexpensive and often works well. The reaction mixture is maintained at a temperature in the range of about 0 to 100° C., typically about 80 to 90° C., and at a pressure typically in the range of about 100 (i.e. atmospheric pressure) to about 500 kPa. Under these conditions the reaction is typically complete in about 1 to 5 h. The product of Formula 7 can be isolated by cooling the mixture, optionally venting excess pressure, distilling to remove excess ammonia and solvent, adding 1 to 2 molar equivalents of mineral acid, preferably aqueous hydrochloric acid, to lower the pH of about 2. If the product of Formula 7 forms solid, it can be collected by filtration, washed with water and dried. If the product of Formula 7 does not form a solid, it can be isolated by extracting the reaction mixture with a suitable water-immiscible solvent such as ether, dichloromethane or ethyl acetate, drying, and evaporating the solvent. This procedure is illustrated in Step E of Example 1.

The fourth subsequent reaction, shown in Scheme 6, prepares a compound of Formula 8 by contacting the compound of Formula 7 with an $R^4$ transfer agent.

Scheme 6

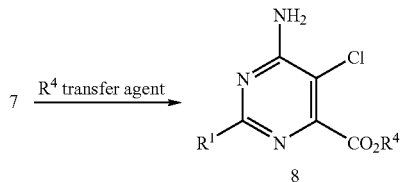

wherein $R^4$ is an optionally substituted carbon moiety.

This method involves conversion of the carboxylic acid group ($CO_2H$) on the compound of Formula 7 to the corresponding ester group ($CO_2R^4$) on the compound of Formula 8. Conversion of carboxylic acids to esters is one of the oldest known transformations in organic chemistry, and an enormous variety of procedures are known. For reviews, see for example, C. A. Buehler and D. E. Pearson, *Survey of Organic Syntheses*, Wiley-Interscience, New York, 1970, pp. 802-827. Most direct procedures involve contacting carboxylic acids with alcohols (e.g., $R^4OH$) in the presence of an acid catalyst or a dehydrating coupling agent, or contacting with compounds providing the alcohol moiety and also consuming the water formed (e.g., orthoesters, carbonates) also typically in the presence of an acid catalyst, or contacting carboxylic acids in the presence of a base with alkylating agent-type chemical compounds in which the $R^4$ radical is bonded to a nucleofuge (e.g., $R^4X$ wherein X is a nucleophilic reaction leaving group, also known as a nucleofuge). Such dehydrating coupling agents as dicyclohexyl carbodiimide, N-(3-dimethylaminopropyl)-N'-ethylcarbodiimide, 1-propanephosphonic acid cyclic anhydride and carbonyl diimidazole are well known in the art, but in view of their cost and the potential interference of the amino group, acid catalysis is the preferred means of preparing compounds of Formula 8 from compounds of Formula 7 and alcohols of formula $R^4OH$. In the method of Scheme 6 compounds such as alcohols of formula $R^4OH$, orthoesters (e.g., $(R^{40})_3CR^a$ wherein $R^a$ is H, $OR^4$ or an optionally substituted carbon moiety), carbonates (e.g., $R^4OC(O)OR^4$) and compounds of formula $R^4X$ are $R^4$ transfer agents, as they provide the $R^4$ moiety needed for transforming the carboxylic acid group of the compound of Formula 7 to the ester group of the compound of Formula 8. As defined in the present disclosure and claims, "$R^4$ transfer agent" means a chemical compound capable of transferring the radical $R^4$ to a carboxylic acid group (i.e. $CO_2H$) or derived carboxylate acid anion (i.e. $CO_2e$) to form the corresponding ester (i.e. $CO_2R^4$). Acid-catalyzed reaction of alcohols of formula $R^4OH$ and corresponding orthoesters of formula $(R^{40})_3CR^a$ and carbonates of formula $R^4OC(O)OR^4$ as the $R^4$ transfer agent work best when they are liquid at the reaction temperature and of comparatively moderate molecular complexity and size (e.g., molecular weights less than 200, preferably less than 150). Reaction with $R^4X$ as the $R^4$ transfer agent works well for $R^4$ groups of both small and large structural size and complexity. Described below are illustrative procedures for this method.

In a procedure using an alcohol of formula $R^4OH$ as the $R^4$ transfer agent with an acid catalyst, a compound of Formula 7 is mixed with typically about 2 to 10 volumes of the alcohol of formula $R^4OH$ and a strong acid as a catalyst. Strong protic acids have a $pK_a$ of less than 3. Examples of useful strong protic acids include phosphoric acid, sulfuric acid, hydrogen chloride, trifluoroacetic acid, p-toluenesulfonic acid, camphorsulfonic acid, methanesulfonic acid and trifluoromethanesulfonic acid. The acids is preferably concentrated and contain as little water as feasible. Hydrogen chloride can be advantageously generated by adding thionyl chloride to the alcohol. Useful strong protic acids also include solid catalysts such as sulfonated polystyrene and perfluorinated ion-exchange resins such as Nafion®. Concentrated sulfuric acid is an inexpensive acid that works well for this method. Besides protic acids, a Lewis acid such as boron trifluoride (e.g., $BF_3$ etherate) can be used as the strong acid. Typically about 2 to 4 molar equivalents of the acid is used relative to the compound of Formula 7, but lesser or greater amounts can be used. The acid is typically added to the reaction mixture last. Addition of the acid can be highly exothermic, so cooling of the reaction mixture may be needed to maintain the desired reaction temperature and prevent excessive boiling of the alcohol. Typically the reaction mixture is maintained at a temperature of about 20 to 100 °C., often around 70 °C. Under these conditions the reaction typically reaches maximum conversion in about 2 to 24 h. The reaction can be accelerated and higher conversions to the ester achieved by distilling out the water that is produced; adding more alcohol and/or acid catalyst may be desirable to compensate for any of the reaction mixture distilled out along with the water. At the completion of the reaction the mixture can be concentrated to remove most of the alcohol ($R^4OH$) if it has a sufficiently low boiling point. Such concentration can also remove volatile acids such as hydrogen chloride. Polymeric acid catalysts can be removed by filtration. The reaction mixture is typically cooled to about 0 to 35 °C. and diluted with water, typically 4 to 8 volumes. The pH is typically adjusted in about 5 to 10, most typically around 7, by adding bases (e.g., alkyl metal and alkaline earth metal hydroxides and carbonates such as sodium hydroxide, calcium hydroxide and sodium carbonate) and also acids (e.g., acetic acid, hydrochloric acid, sulfuric acid) if needed to titrate to a particular pH. If the product of Formula 8 forms a solid, it can be isolated by filtration, washing and drying. If the product of Formula 8 does not form a solid, it can be isolated by extraction with a water-immiscible solvent such as ether, dichloromethane or ethyl acetate, drying the solution and evaporating the solvent. Unreacted starting compound of Formula 7 can often be recovered by acidifying the aqueous mixture to about pH 2 and concentrating the mixture to cause separation of the compound of Formula 7. This procedure is illustrated in Step F1 of Example 1.

In a procedure using an orthoester of formula $(R^4O)_3CR^a$ or a carbonate of formula $R^4OC(O)OR^4$ as the $R^4$ transfer agent, a strong acid is also typically used as a catalyst. The most common orthoesters are orthoformates (i.e. $R^a$ is H) and orthoacetates (i.e. $R^a$ is $CH_3$). At least one molar equivalent of the orthoester of formula $(R^{4O})_3CR^a$ or carbonate of formula $R^4OC(O)OR^4$ is stoichiometrically needed relative to the carboxylic acid of Formula 7 to prepare the ester in the absence of other $R^4$ transfer agents, but about 2 to 8 molar equivalents are typically used to rapidly achieve high yields of ester and to serve as a solvent. Other solvents can also be included in the reaction mixture, such as ethers like tetrahydrofuran and p-dioxane and alcohols of formula $R^4OH$, which can also function as $R^4$ transfer agents under the reaction conditions. If an additional solvent is included in the reaction mixture, it is typically present in up to about 10 volumes relative to the compound of Formula 7. Generally the same acids useful for esterification with alcohols are also useful for esterification with orthoesters and carbonates. Typically about 2 to 4 molar equivalents of the acid is used relative to the compound of Formula 7, but lesser or greater amounts can be used. The acid is typically added to the reaction mixture last. Cooling may be needed during addition of the acid to prevent excessive temperatures. The reaction mixture is typically maintained at a temperature between about 20 and 100° C., most typically between about 70 to 80° C. Under these conditions the reaction is typically complete in about 4 to 24 h. If boiling points allow, excess orthoester, carbonate, alcohol and/or acid catalyst can be removed by distillation or evaporation to give a concentrated residue. The reaction mixture can be worked up and the ester product of Formula 8 isolated using techniques similar to those described for the preceding procedure using an alcohol of formula $R^4OH$ as the $R^4$ transfer agent. This procedure is illustrated in Step F2 of Example 1.

In a procedure using a compound of formula $R^4X$ as the $R^4$ transfer agent, X is a nucleofuge. Compounds of formula $R^4X$ are frequently referred to as alkylating agents although $R^4$ can be optionally substituted carbon moieties besides alkyl. Typically X is the conjugate base of an acid. Common nucleofuges include halogen (e.g., Cl, Br, I), sulfates such as $OS(O)_2OR^4$, and sulfonates such as $OS(O)_2CH_3$ (methanesulfonate), $OS(O)_2CF_3$, $OS(O)_2Ph$-p-$CH_3$ (p-toluenesulfonate). However, nucleofuges useful for forming esters also include pyrocarbonates, silicates and phosphonates. Nucleofuges also include ethers (e.g., $R^4OR^4$) when the $R^4$ transfer agent is an oxonium salt (e.g., $O(R^4)_3{}^\oplus BF_4{}^\ominus$). The compound of Formula 7 is contacted with the compound of formula $R^4X$ typically in a polar solvent such as acetone, acetonitrile or dimethyl sulfoxide (DMSO) and in the presence of a base. Typically about 1 to 2 equivalents each of the compound of formula $R^4X$ and the base are used relative to the compound of Formula 7. Suitable bases include organic amines such as tributylamine and N,N-diisopropylethylamine and inorganic bases such as alkali and alkaline earth metal carbonates, oxides, hydroxides and phosphates (e.g., $Na_2CO_3$, $K_2CO_3$, LiOH, $Li_2O$, NaOH, KOH, $Na_3PO_4$, $K_3PO_4$). The base and the compound of formula $R^4X$ can be added either sequentially or simultaneously. Typically the reaction mixture is maintained at a temperature between about 0 and 120° C., more typically between about 10 and 80° C. Maintaining good agitation is important particularly if the base is an inorganic base not readily soluble in the reaction solvent. The rate of reaction can vary substantially depending upon conditions, but typically the reaction is complete in about 1 to 24 h. To work up the reaction mixture, excess solvent, $R^4X$ and/or base can be removed by evaporation under reduced pressure or distillation, and excess base can be neutralized or removed by extraction with acid. If the compound of Formula 8 is a solid, dilution of the reaction mixture with water (e.g., about 4 to 10 volumes) often results in crystallization of the Formula 8 compound, which can then be collected under filtration, washed and dried. If the compound of Formula 8 does not crystallize from the aqueous mixture, it be extracted using a water-immiscible solvent such as ether, dichloromethane or ethyl acetate, the solution dried, and the solvent evaporated to leave the compound of Formula 8. This procedure is illustrated in Step F3 of Example 1.

Compounds of Formulae 7 and 8 have been reported to have biological utility. In particular, PCT Patent Publication WO 2005/063721 discloses compounds of Formulae 7 and 8 wherein $R^1$ is, for example, cyclopropyl or phenyl substituted with Br or Cl at the phenyl para position, and $R^4$ is, for example, $C_1$-$C_{14}$ alkyl, $C_2$-$C_{14}$ alkoxyalkyl, $C_2$-$C_{14}$ hydroxyalkyl or benzyl, as being useful as herbicides.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. $^1$H NMR and $^{13}$C NMR spectra are reported in ppm downfield from tetramethylsilane; "s" means singlet, "m" means multiplet, "br s" means broad singlet.

EXAMPLE 1

Preparation of methyl 6-amino-5-chloro-2-cyclopropyl-4-pyrimidinecarboxylate

Step A: Preparation of cyclopropanecarboximidamide monohydrochloride

A 1-L reactor equipped with a thermocouple, subsurface gas feed line, hydrogen chloride cylinder, cylinder balance and nitrogen bubbler was flushed with nitrogen and charged with cyclopropanecarbonitrile (100 g, 1.5 mol), methanol (48 g, 1.5 mol) and toluene (400 mL). The reaction mixture was maintained at 15° C. under slight nitrogen positive pressure while feeding anhydrous hydrogen chloride (57 g, 1.55 mol) below the reaction mixture surface over 2 h. Then the reaction mixture was stirred for 16 h at 23° C. Excess hydrogen chloride was purged below the reaction mixture surface and venting the effluent gas through a water scrubber over 2 h. The mixture was cooled to 5° C., and then a solution of ammonia in methanol (240 mL of a 7 M solution, 1.7 mol) was added over 10 minutes while maintaining the temperature below 25° C. After being allowed to stand an additional 1 h, the reaction mixture was distilled at reduced pressure to remove the excess methanol. The product was filtered, washed with toluene (100 mL), and suction-dried to give 170 g (94% yield) of the title compound as a solid.

$^1$H NMR (DMSO-$d_6$) δ 8.8 (br s, 4H), 1.84 (m, 1H), 1.1 (m, 4H).

Step B: Preparation of 2-cyclopropyl-1,6-dihydro-6-oxo-4-pyrimidinecarboxylic acid A 500-mL jacketed reactor equipped with a pH meter, temperature probe and metering addition funnel was charged with denatured ethanol (contained 5% 2-propanol, 30 mL) and water (150 mL). The reaction mixture was stirred while diethyl oxalacetate sodium salt (70 g, 0.33 mol) was added over 10 minutes. A solution of 25% aqueous NaOH (14 g, 56 mL, 0.35 mol) was metered into the stirring vortex over 1 h while maintaining the temperature in a range of 25 to 30 ° C. The reaction mixture was stirred for an additional 30 minutes at 30 ° C., and cyclopropanecarboximidamide monohydrochloride (32 wt % solution in water, 32 g, 0.267 mol) was added. A solution of 25% aqueous NaOH (31 g, 0.19 mol) was added at a temperature ranging from 30 to 35 ° C. over about 1 h so as to maintain the pH in the range of 10.5-11.5. Then the resulting orange mixture was gradually heated to 60 ° C. over a period of 1 h and held at the same temperature for additional 30 minutes. The reaction mixture was cooled to 45-50 ° C., and hydrochloric acid (37 wt. % in water, 50 mL, 0.60 mol) was added over 1 h at about 45 ° C. (CAUTION: foaming) until the pH reached to about 1.5. The reaction mixture was cooled to 5 ° C. and filtered. The resulting wet cake was washed with water (3×20 mL), suction-dried, and dried in a vacuum-oven at 70 ° C. for 16 h to afford 42 g (85% yield) of the title compound as a beige solid (97% purity by HPLC assay) decomposing at 235-236 ° C.

$^1$H NMR (DMSO-$d_6$) δ 6.58 (s, 1H), 1.95 (m, 1H), 1.0 (m, 4H).
$^{13}$C NMR (DMSO-$d_6$) δ 169.2, 169.0, 157.3, 116.8, 17.7, 14.1.

Step C1: Preparation of 5-chloro-2-cyclopropyl-1,6-dihydro-6-oxo-4-pyrimidine-carboxylic acid A 2-L Morton flask with overhead stirrer, thermocouple and addition funnel was charged with 2-cyclopropyl-1,6-dihydro-6-oxo-4-pyrimidinecarboxylic acid (161 g, 0.90 mol), hydrochloric acid (37 wt. % in water, 300 g, 250 mL, 3 mol) and water (400 mL). The reaction mixture was stirred at 5-10° C., and sodium hypochlorite (14 wt % aqueous solution, 522 g, 0.99 mol) was added over 2 h. The reaction mixture was maintained at 10-12° C. for 1 h until a KI-starch paper test using sodium sulfite showed no remaining hypochlorite. The resulting mixture was cooled and filtered. The collected solid was washed with cold water (160 mL), and dried to constant weight in a vacuum-oven at 50° C. to give 169 g (88% yield) of the title compound as a solid melting at 189-190° C.

$^1$H NMR (DMSO-$d_6$) δ 13.4 (br s, 1H), 1.95 (m, 1H), 1.0 (m, 4H).

Step C2: Another Preparation of 5-chloro-2-cyclopropyl-1,6-dihydro-6-oxo-4-pyrimidinecarboxylic acid A 500 mL multi-neck flask with overhead stirrer, thermocouple and addition funnel was charged with 2-cyclopropyl-1,6-dihydro-6-oxo-4-pyrimidinecarboxylic acid (36 g, 0.20 mol), water (70 mL) and 50 wt. % aqueous NaOH (14.4 g, 0.18 mol). The mixture was stirred at 10° C., and 10.3% aqueous NaOCl (160 g, 0.22 mol) was added over 1.5 h with cooling to maintain the reaction mixture at 10° C. The mixture was cooled to 5° C., and sodium sulfite was added until KI-starch paper gave negative test results. Hydrochloric acid (37 wt. % in water, 44.3 g, 0.443 mol) was added at 5° C. over about 30 minutes to lower the pH to 0.8. The mixture was filtered, and the collected solid was washed with cold 1 N HCl (20 mL), and dried to constant weight in a vacuum-oven at 50° C. to give 40.9 g (95% yield) of the title compound as a solid melting at 189-190° C.

Step D1: Preparation of 5,6-dichloro-2-cyclopropyl-4-pyrimidinecarboxylic acid Phosphorus oxychloride (363 g, 221 mL, 2.37 mol) and 5-chloro-2-cyclopropyl-1,6-dihydro-6-oxo-4-pyrimidinecarboxylic acid (169 g, 0.79 mol) were added to a 1-L flask and heated at 90° C. for 5 h. The reaction mixture was cooled to 30° C. and added over 60 minutes into a 2-L jacketed reactor containing a well-stirred mixture of t-butanol (280 mL) and water (750 mL) while maintaining the temperature at 5-10° C. After the addition of the reaction mixture was about 70% complete, the aqueous t-butanol mixture was seeded to initiate crystallization, and the addition of the reaction mixture was continued. At the end of the addition, water (750 mL) was added gradually at 10-15° C., and the mixture was stirred for an additional 1 h. The resulting mixture was cooled to 5° C., filtered, and the collected solid was washed with water (3×50 mL). The resulting wet cake was dried in a vacuum-oven at 60° C. to give 156 g (85% yield) of the title compound as a solid melting at 126-127° C.

$^1$H NMR (DMSO-$d_6$) δ 2.23 (m, 1H), 1.2 (m, 2H), 1.0 (m, 2H).

Step D2: Another Preparation of 5,6-dichloro-2-cyclopropyl-4-pyrimidinecarboxylic acid A 500 mL multi-neck flask with overhead stirrer, thermocouple and condenser was charged with 5-chloro-2-cyclopropyl-1,6-dihydro-6-oxo-4-pyrimidinecarboxylic acid (35.0 g, 0.163 mol), ethyl acetate (105 mL) and N,N-dimethylformamide (1.19 g, 0.016 mol) at room temperature. Thionyl chloride (48.5 g, 0.408 mol) was added at room temperature over 50 minutes, and the reaction mixture was heated at 68° C. for 7 h. The reaction mixture was cooled to 25° C. and added over 30 minutes into a 500-mL multi-neck flask containing water (100 mL) while maintaining the temperature at 10-20° C. The resulting mixture was stirred for additional 30 minutes, and the organic layer was separated from the aqueous layer. The aqueous layer was extracted with additional ethyl acetate (20 mL), and the combined organic layers were washed with water. The organic layer containing 35.0 g (93% yield) of the title product was directly carried over to the next step.

Step E: Preparation of 6-amino-5-chloro-2-cyclopropyl-4-pyrimidinecarboxylic acid A 3-L flask was charged with 5,6-dichloro-2-cyclopropyl-4-pyrimidinecarboxylic acid (280 g, 1.2 mol), ammonia (28 wt % in water, 350 g, 5.76 mol) and water (1.26 L). The reaction mixture was heated at 80° C. for 5 h, and excess water (about 600 mL) was removed by distillation at 50° C./9 kPa. After cooling to 20° C., the reaction mixture was acidified to pH 2 with aqueous hydrochloric acid (132 g, 110 mL, 1.32 mol), cooled to 5° C., and filtered. The filtered wet cake was washed with water (2×200 mL) and dried in a vacuum-oven at 55° C. to give about 270 g of the title compound as a monohydrate, which contained 8.3 wt % of water measured by Karl Fischer titration, and decomposed at 152° C. (after crystallization from hot ethanol).

$^1$H NMR (DMSO-$d_6$) δ 7.4 (br s, 3H), 1.9 (m, 1H), 0.9 (m, 4H).
$^{13}$C NMR (DMSO-$d_6$) δ 172.3, 169.5, 163.9, 158.5, 108.8, 21.1, 13.8.

Step F1: Preparation of methyl 6-amino-5-chloro-2-cyclopropyl-4-pyrimidine-carboxylate A 1-L flask equipped with a nitrogen bubbler connected to a trap and caustic-containing scrubber, an addition funnel, reflux condenser and thermocouple, was charged with 6-amino-5-chloro-2-cyclopropyl-4-pyrimidinecarboxylic acid monohydrate (144 g, 0.62 mol) and methanol (500 mL). Thionyl chloride (185 g, 115 mL, 1.58 mol) was added over about 30 minutes with cooling, and then the reaction mixture was heated at 60° C. for 12 h. The resulting mixture was concentrated at 40-45° C./6 kPa to remove excess methanol (about 300 mL), and the reaction mixture was diluted with water (580 mL). Phenolphthalein (5 mg) was added, and 50% aqueous NaOH (80 g, 1.0 mol) was added dropwise with cooling at 10-25° C. to bring the pH to about 9 as indicated by appearance of pink color. Then just enough 1 N aqueous hydrochloric acid was added to extinguish the pink color. The resulting slurry was cooled to 5° C. and filtered. The filtered wet cake was washed with water and dried to constant weight at 50° C./6 kPa to give 123 g (80% yield) of the title compound with 98% purity by HPLC analysis as a solid melting at 147-148° C.

$^1$H NMR (DMSO-$d_6$) δ 5.4 (br s, 2H), 3.97 (s, 3H), 2.1 (m, 1H), 1.04 (m, 4H).

The remaining filtrate was acidified with hydrochloric acid (37 wt. % in water) to bring the pH to about 2, and then concentrated in vacuo. The resulting slurry was filtered, washed with water, and dried to give 14 g of unreacted 6-amino-5-chloro-2-cyclopropyl-4-pyrimidinecarboxylic acid (10% recovered yield).

Step F2: Another Preparation of methyl 6-amino-5-chloro-2-cyclopropyl-4-pyrimidine-carboxylate A 500 mL multi-neck flask equipped with nitrogen bubbler, addition funnel, reflux condenser, and thermocouple was charged with 6-amino-5-chloro-2-cyclopropyl-4-pyrimidinecarboxylic acid monohydrate (47.8 g, 0.206 mol), methanol (32 g) and dimethyl carbonate (94.5 g, 1.05 mol). Concentrated sulfuric acid (50.0 g, 0.500 mol) was added over about 30 minutes with cooling to maintain the temperature below 60° C., and then the reaction mixture was heated at 70° C. for 10 h. The resulting mixture was cooled to 15° C. and diluted with 250 mL of water. The pH of the reaction mass was raised to 5-8 by adding about 42.7 g (0.534 mol) of 50 wt % aqueous NaOH over 30 minutes with cooling to maintain the temperature in the range of 10-15° C. The resulting slurry was cooled to 5° C. and filtered. The filtered wet cake was washed with water and dried to constant weight at 50° C. to give 43.3 g (93.5% yield) of the title compound with 98% purity as a solid melting at 147-148° C.

Step F3: Another preparation of methyl 6-amino-5-chloro-2-cyclopropyl-4-pyrimidinecarboxylate A 200-mL reactor equipped with a 10-mL jacketed addition funnel below a cold-finger condenser at −10° C., a nitrogen inlet and overhead stirring was charged with tributylamine (20.4 g, 0.11 mol) and DMSO (45 mL). The mixture was stirred at 25° C., and 6-amino-5-chloro-2-cyclopropyl-4-pyrimidinecarboxylic acid monohydrate (23.1 g, 0.1 mol) was added in portions. The reaction mixture was stirred at 30° C. while bromomethane (13.3 g, 8 mL, 0.14 mol) was condensed into the jacketed addition funnel and then added to the reaction mixture over 30 minutes. The mixture was stirred for an additional 3 h and then added over about 30 minutes to a reactor charged with water (200 mL) at 25° C. The resulting slurry was cooled to 5° C. and filtered. The filtered cake was washed with water (2×30 mL) and dried at 60° C. in a vacuum-oven for 16 h to give 18.4 g (81% yield) of the title compound as an off-white solid melting at 147-148° C.

By the present method, the following compounds of Tables 1-4 can be prepared. The following abbreviations are used in the Table which follow: t means tertiary, i means iso, Me means methyl, Et means ethyl, Pr means propyl, i-Pr means isopropyl, c-Pr means cyclopropyl, Bu means butyl, i-Bu means isobutyl, and S(O)$_2$Me means methylsulfonyl.

TABLE 1

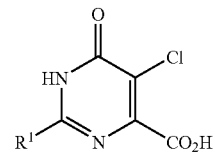

| R$^1$ | R$^1$ | R$^1$ |
|---|---|---|
| i-Pr | 4-I—Ph | 4-MeO—Ph |
| c-Pr | 3-Me—Ph | 4-MeS—Ph |
| 2-Me-c-Pr | 4-Et—Ph | 4-CF$_3$O—Ph |
| t-Bu | 4-CF$_3$—Ph | 3-Br-5-MeO—Ph |
| Ph | 4-Me—Ph | 4-MeS(O)$_2$—Ph |
| 4-Cl—Ph | 3,4-di-Cl—Ph | 4-MeS(O)—Ph |
| 3-Cl—Ph | 2,4-di-Cl—Ph | 1,3-benzodioxol-5-yl |
| 4-Br—Ph | 2-F-4-Cl—Ph | 2-naphthalenyl |
| 4-F—Ph | 3,4-di-Me—Ph | |
| 2-F—Ph | 3-F-4-Me—Ph | |

TABLE 2

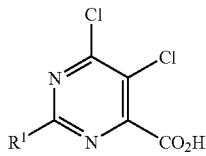

| R¹ | R¹ | R¹ |
|---|---|---|
| i-Pr | 4-I—Ph | 4-MeO—Ph |
| c-Pr | 3-Me—Ph | 4-MeS—Ph |
| 2-Me-c-Pr | 4-Et—Ph | 4-CF₃O—Ph |
| t-Bu | 4-CF₃—Ph | 3-Br-5-MeO—Ph |
| Ph | 4-Me—Ph | 4-MeS(O)₂—Ph |
| 4-Cl—Ph | 3,4-di-Cl—Ph | 4-MeS(O)—Ph |
| 3-Cl—Ph | 2,4-di-Cl—Ph | 1,3-benzodioxol-5-yl |
| 4-Br—Ph | 2-F-4-Cl—Ph | 2-naphthalenyl |
| 4-F—Ph | 3,4-di-Me—Ph | |
| 2-F—Ph | 3-F-4-Me—Ph | |

TABLE 3

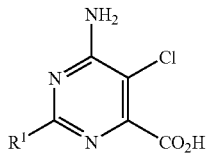

| R¹ | R¹ | R¹ |
|---|---|---|
| i-Pr | 4-I—Ph | 4-MeO—Ph |
| c-Pr | 3-Me—Ph | 4-MeS—Ph |
| 2-Me-c-Pr | 4-Et—Ph | 4-CF₃O—Ph |
| t-Bu | 4-CF₃—Ph | 3-Br-5-MeO—Ph |
| Ph | 4-Me—Ph | 4-MeS(O)₂—Ph |
| 4-Cl—Ph | 3,4-di-Cl—Ph | 4-MeS(O)—Ph |
| 3-Cl—Ph | 2,4-di-Cl—Ph | 1,3-benzodioxol-5-yl |
| 4-Br—Ph | 2-F-4-Cl—Ph | 2-naphthalenyl |
| 4-F—Ph | 3,4-di-Me—Ph | |
| 2-F—Ph | 3-F-4-Me—Ph | |

TABLE 4

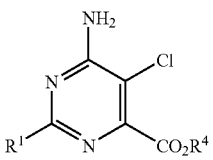

| R¹ | R⁴ |
|---|---|
| c-Pr | CH₂CH₃ |
| c-Pr | CH₃ |
| c-Pr | H |
| c-Pr | i-Pr |
| c-Pr | CH₂CH₂CH₃ |
| c-Pr | CH₂CH₂CH₂CH₃ |
| c-Pr | i-Bu |
| c-Pr | CH₂Ph |
| c-Pr | CH₂CH₂O(n-Bu) |
| c-Pr | CH₂CH₂OCH₂CH₂OCH₃ |
| c-Pr | CH₂CH₂CH₂OH |
| 4-Cl—Ph | H |
| 4-Cl—Ph | i-Pr |
| 4-Cl—Ph | CH₂CH₂CH₃ |
| 4-Cl—Ph | CH₂Ph |
| 3-Cl—Ph | CH₂CH₃ |
| 4-Br—Ph | CH₂CH₃ |
| 4-Br—Ph | CH₃ |
| 4-Br—Ph | H |
| 4-F—Ph | CH₂CH₃ |
| 4-F—Ph | CH₃ |

TABLE 4-continued

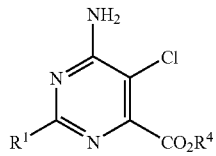

| R¹ | R⁴ |
|---|---|
| 4-F—Ph | H |
| 2-F—Ph | CH₂CH₃ |
| 4-I—Ph | CH₂CH₃ |
| 4-I—Ph | CH₃ |
| 4-Me—Ph | CH₃ |
| 4-Me—Ph | H |
| 3-Me—Ph | CH₃ |
| 4-Et—Ph | CH₂CH₃ |
| c-Pr | (CH₂)₇CH₃ |
| c-Pr | CH(CH₃)(CH₂)₅CH₃ |
| c-Pr | CH₂CH(C₂H₅)(CH₂)₃CH₃ |
| 2-Me-c-Pr | CH₃ |
| i-Pr | CH₂CH₃ |
| i-Pr | CH₃ |
| t-Bu | CH₂CH₃ |
| Ph | CH₂CH₃ |
| Ph | CH₃ |
| 4-Cl—Ph | CH₂CH₃ |
| 4-Cl—Ph | CH₃ |
| 4-CF₃—Ph | CH₂CH₃ |
| 4-CF₃—Ph | CH₃ |
| 3-CF₃—Ph | CH₂CH₃ |
| 4-Me—Ph | CH₂CH₃ |
| 3,4-di-Cl—Ph | CH₂CH₃ |
| 2,4-di-Cl—Ph | CH₂CH₃ |
| 2-F-4-Cl—Ph | CH₂CH₃ |
| 3,4-di-Me—Ph | CH₂CH₃ |
| 3-F-4-Me—Ph | CH₃ |
| 3-F-4-Me—Ph | H |
| 4-MeO—Ph | CH₂CH₃ |
| 4-MeS—Ph | CH₃ |
| 4-CF₃O—Ph | CH₂CH₃ |
| 3-Br-5-MeO—Ph | CH₂CH₃ |
| 4-MeS(O)₂—Ph | CH₃ |
| 4-MeS(O)—Ph | CH₃ |
| 1,3-benzodioxol-5-yl | CH₂CH₃ |
| 2-naphthalenyl | CH₂CH₃ |

What is claimed is:

1. A method for preparing a compound of Formula 1 or 1a

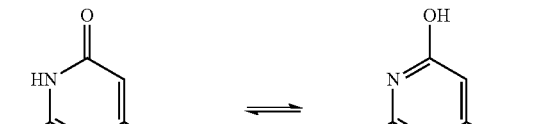

wherein R¹ is optionally substituted cyclopropyl or an optionally substituted phenyl;

comprising the steps of:

(1) contacting a mixture comprising (a) a compound of Formula 2a

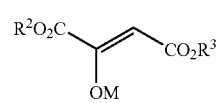

2a wherein M is alkali metal and R² and R³ are independently C₁-C₄ alkyl, (b) a C₁-C₄ alkanol, and (c) a first portion of water, with a solution comprising a first base and a second portion of water, said base being in an amount sufficient to create a first resultant solution having a pH ranging from about 10 to about 14, said first resultant solution comprising a compound of Formula 2b,

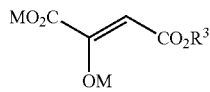

wherein M and R³ are defined as above for Formula 2a;
(2) contacting the first resultant solution comprising the compound of Formula 2b with a compound of Formula 3 or an acid salt thereof or with a solution comprising a compound of Formula 3 or an acid salt thereof,

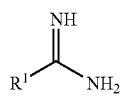

wherein R¹ is defined as above for Formula 1, and a second base in an amount sufficient to create a second resultant solution having a pH ranging from about 9 to about 12, said second resultant solution comprising a salt of the compound of Formula 1; and
(3) adding an acid to the second resultant solution comprising the salt of the compound of Formula 1 to form the compound of Formula 1.

2. The method of claim 1 wherein R¹ is optionally substituted cyclopropyl.

3. The method of claim 1 wherein the first base added in step (1) is an alkali metal hydroxide.

4. The method of claim 3 wherein the alkali metal hydroxide is sodium hydroxide or potassium hydroxide.

5. The method of claim 1 wherein the pH of the first resultant solution in step (1) is in a range of about 11 to about 13.

6. The method of claim 1 wherein the molar ratio of the compound of Formula 3 or an acid salt thereof to the compound of Formula 2a is in a range of 0.7 to about 0.9.

7. The method of claim 1 wherein the second base added in step (2) is an alkali metal hydroxide.

8. The method of claim 7 wherein the alkali metal hydroxide is sodium hydroxide or potassium hydroxide.

9. The method of claim 1 wherein the pH of the second resultant solution in step (2) is in a range of about 10.5 to about 11.5.

10. The method of claim 1 wherein the acid added in step (3) is a mineral acid.

11. The method of claim 10 wherein the acid is sulfuric acid or hydrochloric acid.

12. A method for preparing a compound of Formula 4 or 4a

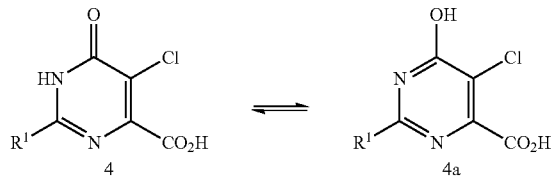

wherein R¹ is optionally substituted cyclopropyl or an optionally substituted phenyl,
comprising the method of claim 1 and a further step comprising contacting the compound of Formula 1 with a chlorinating agent.

13. A method for preparing a compound of Formula 6

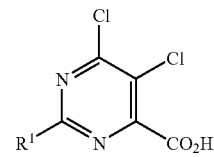

wherein R¹ is optionally substituted cyclopropyl or an optionally substituted phenyl,
comprising the method of claim 12 and a further step comprising contacting the compound of Formula 4 or 4a with a chloride displacement agent.

14. A method for preparing a compound of Formula 7

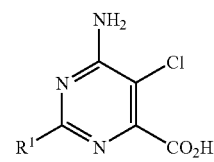

wherein R¹ is optionally substituted cyclopropyl or an optionally substituted phenyl,
comprising the method of claim 13 and a further step comprising contacting the compound of Formula 6 with ammonia.

15. A method of preparing a compound of Formula 8

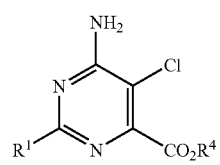

wherein R¹ is optionally substituted cyclopropyl or an optionally substituted phenyl; and R⁴ is $C_1$-$C_{14}$ alkyl, $C_2$-$C_{14}$ alkoxyalkyl, $C_2$-$C_{14}$ hydroxyalkyl or benzyl;
comprising the method of claim 14 and an additional step of contacting the compound of Formula 7 with an R⁴ transfer agent.

16. The method of claim 15 wherein R⁴ is $C_1$-$C_8$ alkyl or $C_2$-$C_8$ alkoxyalkyl.

17. The method of claim 16 wherein R⁴ is $C_1$-$C_4$ alkyl.

18. The method of any one of claims 1-15 or 16-17 wherein R¹ is cyclopropyl.

* * * * *